US009394541B2

(12) United States Patent
Liu et al.

(10) Patent No.: US 9,394,541 B2
(45) Date of Patent: *Jul. 19, 2016

(54) ORAL DELIVERY OF NUCLEIC ACID-BASED GENE INTERFERING AGENTS BY *SALMONELLA*

(71) Applicant: The Regents of the University of California, Oakland, CA (US)

(72) Inventors: Fenyong Liu, Berkeley, CA (US); Sangwei Lu, Kensington, CA (US); Yong Bai, Albany, CA (US); Hao Gong, El Cerrito, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/569,118

(22) Filed: Dec. 12, 2014

(65) Prior Publication Data

US 2015/0197748 A1    Jul. 16, 2015

Related U.S. Application Data

(63) Continuation of application No. 13/753,331, filed on Jan. 29, 2013, now Pat. No. 8,921,335.

(60) Provisional application No. 61/593,006, filed on Jan. 31, 2012.

(51) Int. Cl.
*A61K 48/00* (2006.01)
*C12N 15/113* (2010.01)
*A61K 35/74* (2015.01)

(52) U.S. Cl.
CPC .............. *C12N 15/113* (2013.01); *A61K 35/74* (2013.01); *A61K 48/00* (2013.01); *C12N 2310/126* (2013.01); *C12N 2310/14* (2013.01); *C12N 2330/50* (2013.01)

(58) Field of Classification Search
None
See application file for complete search history.

(56) References Cited

PUBLICATIONS

Bai; et al. "*Salmonella*-mediated delivery of RNase P-based ribozymes for inhibition of viral gene expression and replication in human cells", Proc Natl Acad Sci USA (Apr. 2010), 107(16):7269-7274.
Bertrand; et al. "The expression cassette determines the functional activity of ribozymes in mammalian cells by controlling their intracellular localization", RNA (Jan. 1997), 3(1):75-88.
Levine; et al. "Safety, infectivity, immunogenicity, and in vivo stability of two attenuated auxotrophic mutant strains of *Salmonella typhi*, 541Ty and 543Ty, as live oral vaccines in humans", J Clin Invest (Mar. 1987), 79(3):888-902.
Levine; et al. "Typhoid vaccines ready for implementation", N Engl J Med (Jul. 2009), 61(4):403-405.
Liu; et al. "Inhibition of viral gene expression by the catalytic RNA subunit of RNase P from *Escherichia coli*", Genes Dev (Feb. 1995), 15;9(4):471-480.
Mocarski; et al. "Cytomegaloviruses", In Fields virology, (2007), (5):2701-2772. Philadelphia, PA.
Paglia; et al."In vivo correction of genetic defects of monocyte/macrophages using attenuated *Salmonella* as oral vectors for targeted gene delivery", Gene Ther (Oct. 2000), 7(20):1725-1730.
Trang; et al. "Effective inhibition of human cytomegalovirus gene expression and replication by a ribozyme derived from the catalytic RNA subunit of RNase P from *Escherichia coli*", Proc Natl Acad Sci USA (May 2000), 97 (11):5812-5817.
Bai, Young, In vivo Delivery of Catalytic RNase P Ribozyme as an Antiviral Agent, UC Berkeley: Comparative Biochemestry, 2010. Retrieved from: http://escholarship.org/uc/item/5kx3k87c.
Trang, Phong et al., Effective inhibition of herpes simplex virus 1 gene expression and growth by engineered RNase P ribozyme, Nucleic Acids Research, 2001, vol. 29:5071-5078, Oxford University Press.
Bhuyan, Prakash et al., Short Interfering RNA-Mediated Inhibition of Herpes Simplex Virus Type 1 Gene Expression and Function during Infection of Human Keratinocytes, Journal of Virology, 2004, vol. 78:10276-10281.
Yang, Nan et al., Oral administration of attenuated S. typhimurium carrying shRNA-expressing vectors as a cancer therapeutic, Cancer Biology & Therapy, 2008, vol. 7:1 147-153.
Nguyen, Thu et al., Bacterial Vectors for RNAi Deliver, Patho-Biotechnology, 2008, pp. 121-125.

*Primary Examiner* — Kimberly Chong
(74) *Attorney, Agent, or Firm* — Pamela J. Sherwood; Bozicevic, Field & Francis LLP

(57) ABSTRACT

The present invention provides vectors, including a novel attenuated strain of *Salmonella*, for efficient gene transfer into an animal, e.g. a mammalian host.

6 Claims, 6 Drawing Sheets

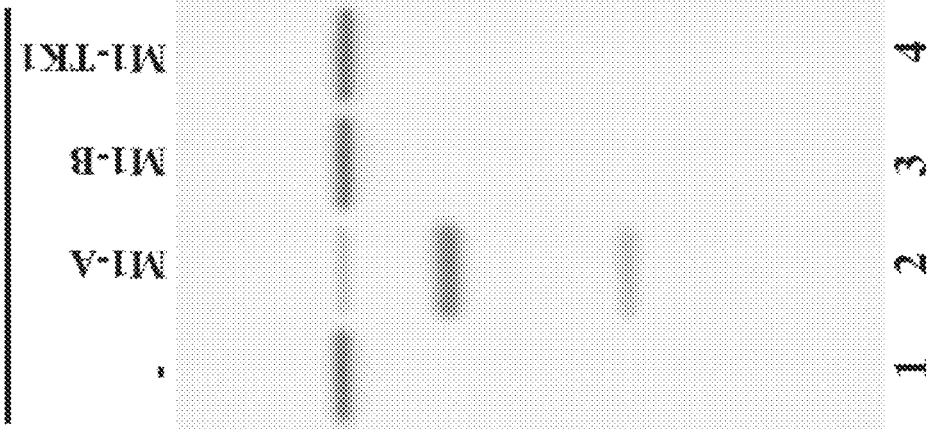
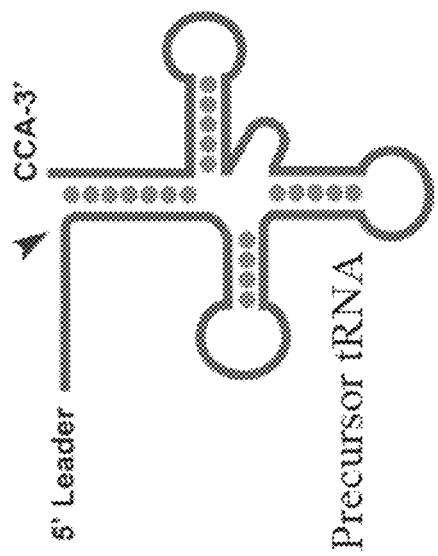
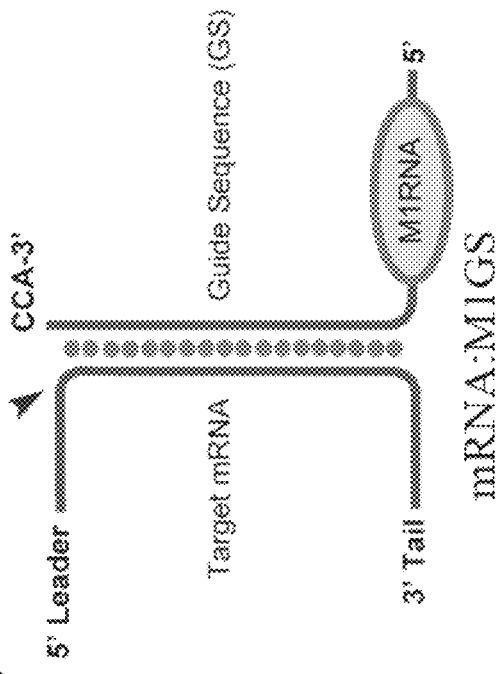
FIG. 1A
FIG. 1B
FIG. 1C

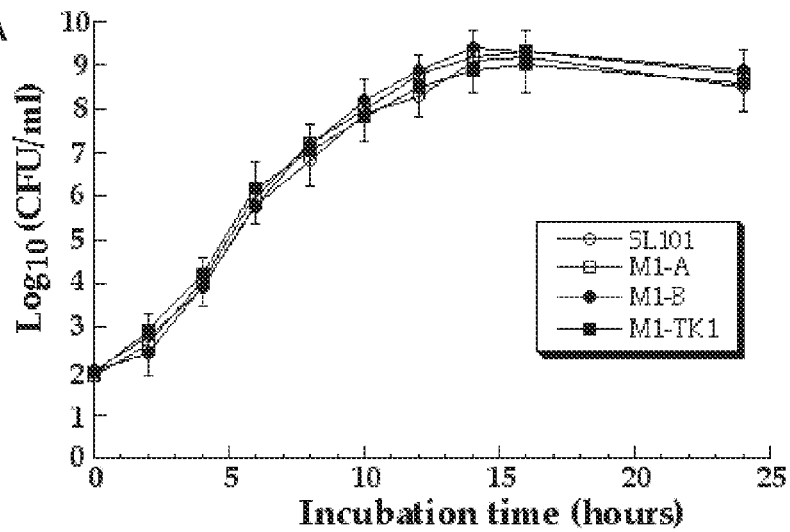
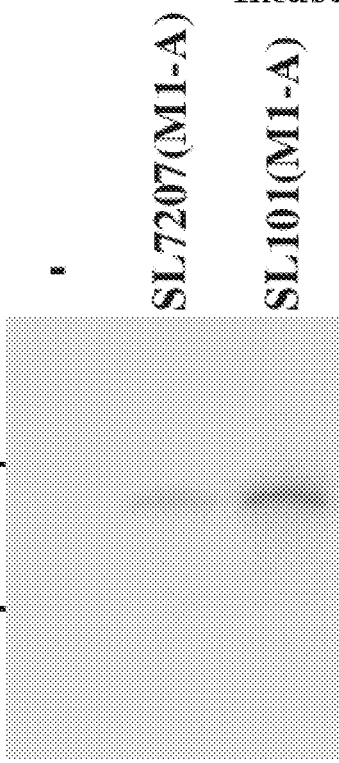
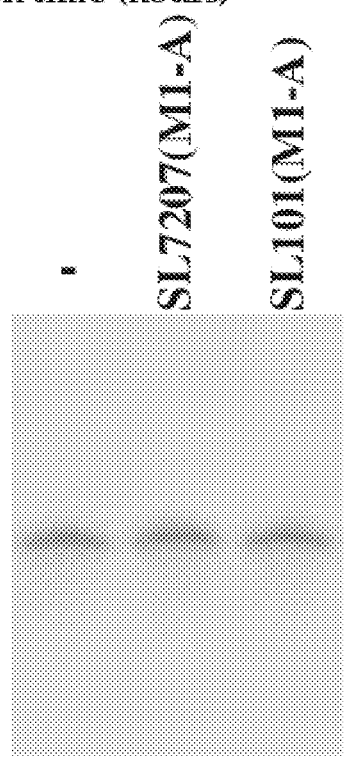
FIG. 2B  FIG. 2C

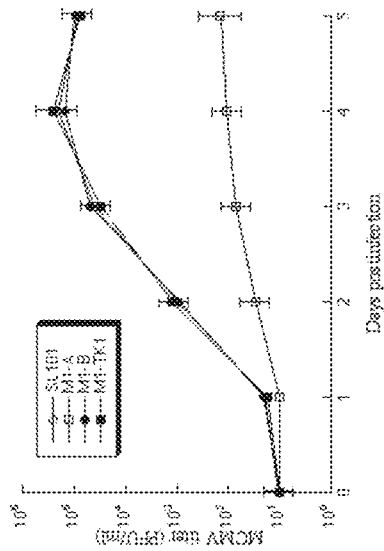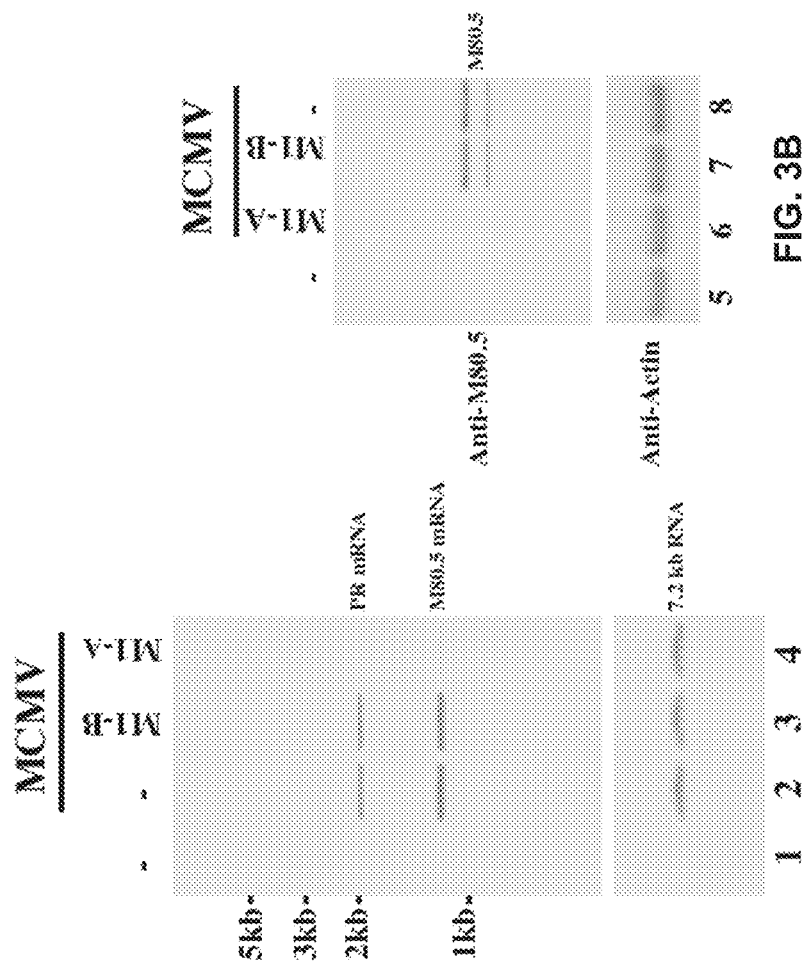
FIG. 3A  FIG. 3B  FIG. 3C

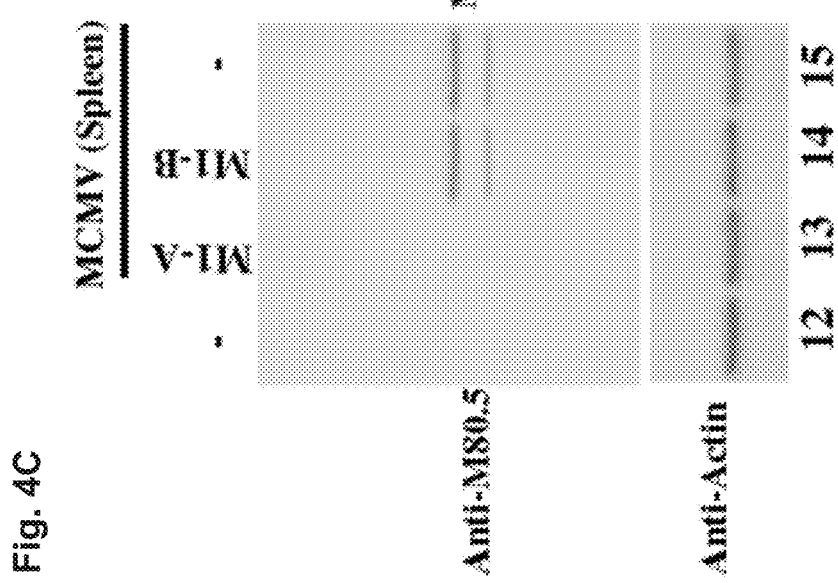

US 9,394,541 B2

ORAL DELIVERY OF NUCLEIC ACID-BASED GENE INTERFERING AGENTS BY *SALMONELLA*

GOVERNMENT SUPPORT

This invention was made with Government support under contracts RO1-AI1041927 and R56-AI091536 awarded by the National Institutes of Health. The government has certain rights in this invention.

SUMMARY OF THE INVENTION

Safe, effective, and tissue-specific delivery is a central issue for the therapeutic application of nucleic acid-based gene interfering agents, such as ribozymes and small interfering RNAs (siRNAs). The present invention provides vectors, including a novel attenuated strain of *Salmonella*, for efficient gene transfer into an animal, e.g. a mammalian host.

BRIEF DESCRIPTION OF THE DRAWINGS

FIG. 1A-FIG. 1B Schematic representation of a natural substrate (ptRNA) FIG. 1A and a complex formed between a M1GS RNA and its mRNA substrate FIG. 1B. FIG. 1C Cleavage of the M80.5 mRNA substrate by M1GS RNA in vitro. The substrate (20 nM) was incubated alone (lane 1), with 5 nM of M1-A (lanes 2), M1-B (lane 3), or M1-TK1 (lane 4). The cleavage products were separated on a denaturing polyacrylamide gel.

FIG. 2A Analysis of growth in LB broth of *Salmonella* strain SL101 and its derivatives that carried constructs pU6-M1-A, pU6-M1-B, and pU6-M1-TK1. FIG. 2B-FIG. 2C Northern analyses of the expression of M1GS ribozymes in mouse J774 macrophages that were treated with strain SL101 carrying the empty vector pU6 (−, lane 1, 4) and pU6-M1-A (lanes 3 and 6), or with strain SL7207 carrying pU6-M1-A (lanes 2 and 5). The levels of the mouse RNase P RNA subunit (mP1 RNA) were used as the internal control FIG. 2C.

FIG. 3A-FIG. 3B Expression levels of MCMV mRNAs FIG. 3A and proteins FIG. 3B. Mouse J774 cells were first treated with *Salmonella* carrying the empty vector pU6 (−, lanes 1-2, 5, 8) or constructs that contained the sequence of M1-B (lanes 3 and 7) and M1-A (lanes 4 and 6). The cells were then either mock-infected (lanes 1 and 5) or infected with MCMV (lanes 2-4 and 6-8) and harvested at 48 hours post-infection. The levels of the MCMV 7.2 kb transcript and mouse actin protein were used as the internal controls in Northern FIG. 3A and Western FIG. 3B analyses, respectively. FIG. 3C Growth of MCMV in mouse J774 cells that were treated with SL101 carrying pU6 (SL101), pU6-M1-A (M1-A), pU6-M1-B (M1-B), or pU6-M1-TK1 (M1-TK1).

DETAILED DESCRIPTION OF THE INVENTION

Figure 4A:
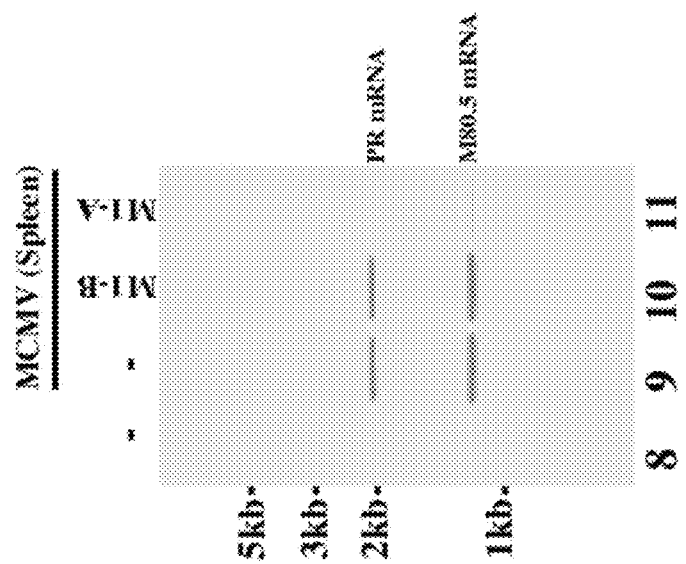
FIG. 4A Expression of M1GS RNA, viral mRNAs FIG. 4B, and proteins in vivo FIG. 4C. Spleens, livers, and lungs were isolated from SCID mice that were intragastrically inoculated with SL101 carrying different constructs and either mock-infected (lanes 1-7, 8, and 12) or infected with MCMV (lanes 9-11 and 13-15), and were harvested at 14 days post-infection. Northern and Western analyses were carried out using RNA FIG. 4A-FIG. 4B or protein samples FIG. 4C isolated from different organs of animals that received SL101 carrying pU6 (−, lanes 1, 8-9, 12, and 15), pU6-M1-B (lanes 3, 5, 7, 10, and 14), or pU6-M1-A (lanes 2, 4, 6, 11, and 13). The levels of the mouse RNase P RNA (mP1) and actin protein were used as the internal controls.

Before the present methods and compositions are described, it is to be understood that this invention is not limited to particular method or composition described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited. It is understood that the present disclosure supersedes any disclosure of an incorporated publication to the extent there is a contradiction.

It must be noted that as used herein and in the appended claims, the singular forms "a", "an", and "the" include plural referents unless the context clearly dictates otherwise. Thus, for example, reference to "a cell" includes a plurality of such cells and reference to "the peptide" includes reference to one or more peptides and equivalents thereof, e.g. polypeptides, known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Definitions

By "comprising" it is meant that the recited elements are required in the composition/method/kit, but other elements may be included to form the composition/method/kit etc. within the scope of the claim. By "consisting essentially of", it is meant a limitation of the scope of composition or method described to the specified materials or steps that do not materially affect the basic and novel characteristic(s) of the subject invention. By "consisting of", it is meant the exclusion from the composition, method, or kit of any element, step, or ingredient not specified in the claim.

The terms "treatment", "treating" and the like are used herein to generally mean obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. "Treatment" as used herein covers any treatment of a disease in a mammal, and includes: (a) preventing the disease from occurring in a subject which may be predisposed to the disease but has not yet been diagnosed as having it; (b) inhibiting the disease, i.e., arresting its development; or (c) relieving the disease, i.e., causing regression of the disease. The therapeutic agent may be administered before, during or after the onset of disease or injury. The treatment of ongoing disease, where the treatment stabilizes or reduces the undesirable clinical symptoms of the patient, is of particular interest. Such treatment is desirably performed prior to complete loss of function in the affected tissues. The subject therapy will desirably be administered during the symptomatic stage of the disease, and in some cases after the symptomatic stage of the disease.

The terms "individual," "subject," "host," and "patient," are used interchangeably herein and refer to any mammalian subject for whom diagnosis, treatment, or therapy is desired, particularly humans.

General methods in molecular and cellular biochemistry can be found in such standard textbooks as Molecular Cloning: A Laboratory Manual, 3rd Ed. (Sambrook et al., CSH Laboratory Press 2001); Short Protocols in Molecular Biology, 4th Ed. (Ausubel et al. eds., John Wiley & Sons 1999); Protein Methods (Bollag et al., John Wiley & Sons 1996); Nonviral Vectors for Gene Therapy (Wagner et al. eds., Academic Press 1999); Viral Vectors (Kaplift & Loewy eds., Academic Press 1995); Immunology Methods Manual (I. Lefkovits ed., Academic Press 1997); and Cell and Tissue Culture: Laboratory Procedures in Biotechnology (Doyle & Griffiths, John Wiley & Sons 1998), the disclosures of which are incorporated herein by reference. Reagents, cloning vectors, and kits for genetic manipulation referred to in this disclosure are available from commercial vendors such as BioRad, Stratagene, Invitrogen, Sigma-Aldrich, and ClonTech.

As used herein, a "target cell" is a virus infected cell. Usually a target cell is a mammalian cell, preferably a human cell.

The term "gene" is well understood in the art and includes polynucleotides encoding a polypeptide. In addition to the polypeptide coding regions, a gene may include non-coding regions including, but not limited to, introns, transcribed but untranslated segments, and regulatory elements upstream and downstream of the coding segments.

The terms "polypeptide", "peptide" and "protein" are used interchangeably to refer to polymers of amino acids of any length. These terms also include proteins that are post-translationally modified through reactions that include glycosylation, acetylation and phosphorylation.

As used herein, "cytotoxicity" is a term well understood in the art and refers to a state in which one or more of a cell's usual biochemical or biological functions are perturbed. These activities include, but are not limited to, metabolism, cellular replication, DNA replication, transcription, translation, and uptake of molecules. "Cytotoxicity" includes cell death and/or cytolysis. Assays are known in the art which indicate cytotoxicity, such as dye exclusion, 3H-thymidine uptake, and plaque assays.

A "biological sample" encompasses a variety of sample types obtained from an individual and can be used in a diagnostic or monitoring assay. The definition encompasses blood and other liquid samples of biological origin, solid tissue samples such as a biopsy specimen or tissue cultures or cells derived therefrom and the progeny thereof. The definition also includes samples that have been manipulated in any way after their procurement, such as by treatment with reagents, solubilization, or enrichment for certain components, such as proteins or polynucleotides. The term "biological sample" encompasses a clinical sample, and also includes cells in culture, cell supernatants, cell lysates, serum, plasma, biological fluid, and tissue samples.

An "individual" is a vertebrate, preferably a mammal, more preferably a human. Mammals include, but are not limited to, rodents, primates, farm animals, sport animals, and pets.

An "effective amount" is an amount sufficient to effect beneficial or desired clinical results. An effective amount can be administered in one or more administrations. For purposes of this invention, an effective amount of a nucleic acid-based gene interfering agent is an amount that is sufficient to palliate, ameliorate, stabilize, reverse, slow or delay the progression of the disease state.

In the present methods, nucleic acid-based gene interfering agent may be produced by recombinant methods. The nucleic acid is inserted into a replicable vector for expression. Many such vectors are available. The vector components generally include, but are not limited to, one or more of the following: an origin of replication, one or more marker genes, an enhancer element, a promoter, and a transcription termination sequence. In some embodiments, for example in the utilization of bacterial delivery agents such as *Salmonella*, the gene may be integrated into the host cell chromosome.

Expression vectors usually contain a selection gene, also termed a selectable marker. This gene encodes a protein necessary for the survival or growth of transformed host cells grown in a selective culture medium. Host cells not transformed with the vector containing the selection gene will not survive in the culture medium. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media.

Expression vectors will contain a promoter that is recognized by the host organism and is operably linked to the nucleic acid-based gene interfering agent sequence. Promoters are untranslated sequences located upstream (5') to the start codon of a structural gene (generally within about 100 to 1000 bp) that control the transcription n of particular nucleic acid sequence to which they are operably linked. In bacterial cells, the region controlling overall regulation can be referred to as the operator. Promoters typically fall into two classes, inducible and constitutive. Inducible promoters are promoters that initiate increased levels of transcription from DNA under their control in response to some change in culture conditions, e.g., the presence or absence of a nutrient or a change in temperature. A large number of promoters recognized by a variety of potential host cells are well known.

Promoters suitable for use with prokaryotic hosts include the β-lactamase and lactose promoter systems, alkaline phosphatase, a tryptophan (trp) promoter system, hybrid promoters such as the tac promoter, and starvation promoters (Matin, A. (1994) Recombinant DNA Technology II, Annals of New York Academy of Sciences, 722:277-291). However, other known bacterial promoters are also suitable. Such nucleotide sequences have been published, thereby enabling a skilled worker operably to ligate them to a DNA coding sequence. Promoters for use in bacterial systems also will contain a Shine-Dalgarno (S.D.) sequence operably linked to the coding sequence.

Construction of suitable vectors containing one or more of the above-listed components employs standard ligation techniques. Isolated plasmids or DNA fragments are cleaved, tailored, and re-ligated in the form desired to generate the plasmids required. For analysis to confirm correct sequences in plasmids constructed, the ligation mixtures are used to transform host cells, and successful transformants selected by ampicillin or tetracycline resistance where appropriate. Plasmids from the transformants are prepared, analyzed by restriction endonuclease digestion, and/or sequenced.

In some embodiments of the invention, the expression vector is a plasmid or bacteriophage vector suitable for use in *Salmonella*, and the nucleic acid-based gene interfering agentis provided to a patient through expression by an attenuated *Salmonella* cell administered to the patient. The term "plasmid" as used herein refers to any nucleic acid encoding an expressible gene and includes linear or circular nucleic acids and double or single stranded nucleic acids. The nucleic acid can be DNA or RNA and may comprise modified nucleotides or ribonucleotides, and may be chemically modified by such means as methylation or the inclusion of protecting groups or cap- or tail structures. Replicating plasmids can be identified using standard assays including the standard replication assay of Ustav and Stenlund (1991).

The invention includes methods for preparing pharmaceutical compositions for modulating the expression or activity of a nucleic acid of interest. Such methods comprise formulating a pharmaceutically acceptable carrier with an agent that modulates expression or activity of an active compound of interest. Such compositions can further include additional active agents. Thus, the invention further includes methods for preparing a pharmaceutical composition by formulating a pharmaceutically acceptable carrier with an agent encodes the nucleic acid of interest and one or more additional active compounds.

A pharmaceutical composition of the invention is formulated to be compatible with its intended route of administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersions. For intravenous administration, suitable carriers include physiological saline, bacteriostatic water, Cremophor EL™ (BASF; Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed.

Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from a pressurized container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

Of interest as agents are RNAi agents. By RNAi agent is meant an agent that modulates expression of an RNA by a RNA interference mechanism. The RNAi agents employed in one embodiment of the subject invention are small ribonucleic acid molecules (also referred to herein as interfering ribonucleic acids), i.e., oligoribonucleotides, that are present in duplex structures, e.g., two distinct oligoribonucleotides hybridized to each other or a single ribooligonucleotide that assumes a small hairpin formation to produce a duplex structure. By oligoribonucleotide is meant a ribonucleic acid that does not exceed about 100 nt in length, and typically does not exceed about 75 nt length, where the length in certain embodiments is less than about 70 nt. Where the RNA agent is a duplex structure of two distinct ribonucleic acids hybridized to each other, e.g., an siRNA, the length of the duplex structure typically ranges from about 15 to 30 bp, usually from about 15 to 29 bp, where lengths between about 20 and 29 bps, e.g., 21 bp, 22 bp, are of particular interest in certain embodiments. Where the RNA agent is a duplex structure of a single ribonucleic acid that is present in a hairpin formation, i.e., a shRNA, the length of the hybridized portion of the hairpin is typically the same as that provided above for the siRNA type of agent or longer by 4-8 nucleotides. The weight of the RNAi agents of this embodiment typically ranges from about 5,000 daltons to about 35,000 daltons, and in many embodiments is at least about 10,000 daltons and less than about 27,500 daltons, often less than about 25,000 daltons.

dsRNA can be prepared according to any of a number of methods that are known in the art, including in vitro and in vivo methods, as well as by synthetic chemistry approaches. Examples of such methods include, but are not limited to, the methods described by Sadher et al. (Biochem. Int. 14:1015, 1987); by Bhattacharyya (Nature 343:484, 1990); and by Livache, et al. (U.S. Pat. No. 5,795,715), each of which is incorporated herein by reference in its entirety. Single-stranded RNA can also be produced using a combination of enzymatic and organic synthesis or by total organic synthesis. The use of synthetic chemical methods enables one to introduce desired modified nucleotides or nucleotide analogs into the dsRNA. dsRNA can also be prepared in vivo according to a number of established methods (see, e.g., Sambrook, et al. (1989) Molecular Cloning: A Laboratory Manual, 2nd ed.; Transcription and Translation (B. D. Hames, and S. J. Higgins, Eds., 1984); DNA Cloning, volumes I and II (D. N. Glover, Ed., 1985); and Oligonucleotide Synthesis (M. J. Gait, Ed., 1984, each of which is incorporated herein by reference in its entirety).

In certain embodiments, instead of the RNAi agent being an interfering ribonucleic acid, e.g., an siRNA or shRNA as described above, the RNAi agent may encode an interfering ribonucleic acid, e.g., an shRNA, as described above. In other words, the RNAi agent may be a transcriptional template of the interfering ribonucleic acid. In these embodiments, the transcriptional template is typically a DNA that encodes the interfering ribonucleic acid. The DNA may be present in a vector, where a variety of different vectors are known in the art, e.g., a plasmid vector, a viral vector, etc.

Alternative the active agent may be a ribozyme. The term "ribozyme" as used herein for the purposes of specification and claims is interchangeable with "catalytic RNA" and means an RNA molecule that is capable of catalyzing a chemical reaction.

EXPERIMENTAL

In this study, we constructed a functional RNase P-based ribozyme (M1GS RNA) that targets the overlapping mRNA region of M80.5 and protease, two murine cytomegalovirus (MCMV) proteins essential for viral replication. In addition, a novel attenuated strain of *Salmonella*, which exhibited efficient gene transfer activity and little cytotoxicity/pathogenicity in mice, was constructed and used for delivery of anti-MCMV ribozyme. In MCMV-infected macrophages treated with the constructed attenuated *Salmonella* strain carrying the functional M1GS RNA construct, we observed an 80-85% reduction in the expression of M80.5/protease and a 2,500-fold reduction in viral growth. Oral inoculation of the attenuated *Salmonella* strain in mice efficiently delivered antiviral M1GS RNA into spleens and livers, leading to substantial expression of the ribozyme without causing significant adverse effects in the animals. Furthermore, the MCMV-infected mice that were treated orally with *Salmonella* carrying the functional M1GS sequence displayed reduced viral gene expression, decreased viral titers and improved survival compared to the untreated mice or mice treated with *Salmonella* containing control ribozyme sequences. Our results provide the first direct evidence that oral delivery of M1GS RNA by *Salmonella*-based vectors effectively inhibits viral gene expression and replication in mice. Moreover, this study demonstrates the utility of *Salmonella*-mediated oral delivery of RNase P ribozyme for gene targeting applications in vivo.

Introduction

Cytomegalovirus (CMV), a member of the herpesvirus family that includes herpes simplex virus 1 (HSV-1) and Epstein-Barr virus, is the leading viral cause of mental retardation in newborns and causes life-threatening complications in immunocompromised individuals including AIDS patients (Mocarski, E. S., Shenk, T. & Pass, R. F., Fields Virology pp. 2701-2772). The emergence of drug-resistant strains of CMV has posed a need to develop new antiviral agents and treatment procedures. Macrophages and their progenitor cells, including monocytes, represent the major reservoir for CMV as this virus can establish both primary and latent infections in these cell (Mocarski, E. S., Shenk, T. & Pass, R. F., Fields Virology pp. 2701-2772). Thus, blocking CMV infection and replication in macrophages is central for treatment and prevention of CMV-associated diseases. A suitable animal model for human CMV infection is lacking due to the inability of this virus to propagate in non-human cells (Mocarski, E. S., Shenk, T. & Pass, R. F., Fields Virology pp. 2701-2772). Murine cytomegalovirus (MCMV) infection of mice resembles its human counterpart with respect to pathogenesis, and thus represents an excellent animal model for studying CMV infection in vivo and for screening new drugs and developing novel treatment strategies (Mocarski, E. S., Shenk, T. & Pass, R. F., Fields Virology pp. 2701-2772).

Nucleic acid-based gene interference technologies, including ribozymes and small interfering RNAs (siRNAs), represent promising gene-targeting strategies for specific inhibition of mRNA sequences of choice (Castanotto, D. & Rossi, J. J., Nature 457, 426-33) (Scherer, L. J. & Rossi, J. J., Nat Biotechnol 21, 1457-65). For example, siRNAs effectively induce the RNA interference (RNAi) pathway to block gene expression in vitro and in vivo (Castanotto, D. & Rossi, J. J., Nature 457, 426-33). Altman and colleagues have previously shown that RNase P of *Escherichia coli* contains a catalytic RNA subunit (M1 RNA) (Gopalan, V. & Altman, S., The RNA World pp. Chapter 6.1) (Guerrier-Takada, C., Gardiner, K., Marsh, T., Pace, N. & Altman, S., Cell 35, 849-57), which can be engineered into a sequence-specific ribozyme (M1GS RNA) (FIG. 1A-B) (Forster, A. C. & Altman, S., Science 249, 783-6) (Liu, F. & Altman, S., *Escherichia coli*. Genes dev 9, 471-80). M1GS RNAs efficiently cleave target cellular and viral mRNAs in vitro and block their expression in cultured cells (Cobaleda, C. & Sanchez-Garcia, I., Blood 95, 731-737) (Trang, P., Lee, M., Nepomuceno, E., Kim, J., Zhu, H. & Liu, F., Proc Natl Acad Sci USA 97, 5812-7). The M1 GS-based strategy represents a distinctive nucleic acid-based interference approach because of the use of M1 RNA, an efficient naturally occurring RNA catalyst found in nature (Gopalan, V. & Altman, S., The RNA World pp. Chapter 6.1).

A fundamental challenge to use nucleic acid-based gene interfering approaches for gene therapy is to deliver the gene interfering agents to appropriate cells in a way that is tissue/cell specific, efficient and safe. Many of the currently used vectors are based on attenuated or modified viruses, or synthetic vectors in which complexes of DNA, proteins, and/or lipids are formed in particles, and tissue-specific vectors have been only partially obtained by using carriers that specifically target certain cell types (Robbins, P. D. & Ghivizzani, S. C., Pharmacol Ther 80, 35-47) (Vassaux, G., Nitcheu, J., Jezzard, S. & Lemoine, N. R., J Pathol 208, 290-8). As such, efficient and targeted delivery of M1GS sequences to specific cell types and tissues in vivo is central to developing this technology for gene targeting applications.

Invasive bacteria, such as *Salmonella*, possess the ability to enter and transfer genetic material to human cells, leading to the efficient expression of transferred genes (Darji, A., Guzman, C. A., Gerstel, B., Wachholz, P., Timmis, K. N., Wehland, J., Chakraborty, T. & Weiss, S., *S. typhimurium*. Cell 91, 765-75) (Grillot-Courvalin, C., Goussard, S. & Courvalin, P., Curr Opin Biotechnol 10, 477-81) (Dietrich, G., Bubert, A., Gentschev, I., Sokolovic, Z., Simm, A., Catic, A., Kaufmann, S. H., Hess, J., Szalay, A. A. & Goebel, W., *Listeria monocytogenes*. Nat Biotechnol 16, 181-5) (Hoiseth, S. K. & Stocker, B. A., Nature 291, 238-9). Attenuated *Salmonella* strains have been shown to function as a carrier system for delivery of nucleic acid-based vaccines and anti-tumor transgenes (Darji, A., Guzman, C. A., Gerstel, B., Wachholz, P., Timmis, K. N., Wehland, J., Chakraborty, T. & Weiss, S., *S. typhimurium*. Cell 91, 765-75) (Grillot-Courvalin, C., Goussard, S. & Courvalin, P., Curr Opin Biotechnol 10, 477-81) (Paglia, P., Terrazzini, N., Schulze, K., Guzman, C. A. & Colombo, M. P., Gene Ther 7, 1725-30) (Yang, N., Zhu, X., Chen, L., Li, S. &

Ren, D., Cancer Biol Ther 7, 145-51). In these studies, plasmid constructs, which contained the transgenes under the control of a eukaryotic expression promoter, were introduced to *Salmonella*. These attenuated strains can target specific cells such as dendritic cells, macrophages, and epithelial cells, leading to efficient transgene expression, although the mechanism of how the plasmid DNA from a bacterial vector is transferred to the host is not completely understood (Grillot-Courvalin, C., Goussard, S. & Courvalin, P., Curr Opin Biotechnol 10, 477-81). *Salmonella*-based vectors are low cost and easy to prepare. Furthermore, they can be administrated orally in vivo, a non-invasive delivery route with significant advantage. Thus, *Salmonella* may represent a promising gene delivery agent for gene therapy. Macrophages represent the major in vivo reservoir for *Salmonella* following their systemic dissemination and therefore, are considered an optimal target for any *Salmonella*-based gene therapy (Grillot-Courvalin, C., Goussard, S. & Courvalin, P., Curr Opin Biotechnol 10, 477-81) (Paglia, P., Terrazzini, N., Schulze, K., Guzman, C. A. & Colombo, M. P., Gene Ther 7, 1725-30). However, it has not been reported whether *Salmonella* can efficiently deliver ribozymes, such as RNase P ribozymes, for expression in animals. Equally unclear is whether *Salmonella*-mediated delivery of ribozymes would also function to inhibit gene expression in vivo.

In this study, we have constructed a new attenuated strain of *Salmonella*, SL101, which exhibited high gene transfer activity and low cytotoxicity/pathogenicity. Using MCMV infection of mice as the model, we demonstrated that oral inoculation of SL101 in animals efficiently delivered RNase P-based ribozyme sequence into specific organs, leading to substantial expression of ribozyme and effective inhibition of viral infection and pathogenesis. M1 GS ribozymes were constructed to target the mRNA coding for MCMV protein M80.5. The coding sequence of M80.5 is completely within the 3' coding sequence of viral protease (PR). Thus, our ribozyme would be expected to target both M80.5 and PR, which are essential for MCMV capsid assembly and replication (Mocarski, E. S., Shenk, T. & Pass, R. F., Fields Virology pp. 2701-2772). Our results provide the first direct evidence that ribozymes expressed following targeted gene transfer with *Salmonella*-based vectors are highly active in blocking viral infection in animals. Moreover, these results demonstrate the utility of *Salmonella*-assisted oral delivery of RNase P ribozymes as a general approach for gene targeting applications in vivo.

Results

Gene delivery of M1 GS sequence for expression in cultured cells by constructed attenuated *Salmonella*. To achieve efficient targeting, it is crucial to choose a target region that is accessible to binding of the M1 GS ribozyme since most mRNAs inside cells are usually present either in folded conformations or associated with proteins. We have used an in vivo mapping approach with dimethyl sulphate (DMS) (Liu, F. & Altman, S., *Escherichia coli*. Genes dev 9, 471-80) to determine the accessibility of the region of the M80.5 mRNA in MCMV-infected cells and have chosen a highly accessible region as the cleavage site for M1GS RNA. We constructed functional ribozyme M1-A by linking the 3' terminus of M1 RNA with a guide sequence of 18 nucleotides that is complementary to the targeted M80.5 mRNA sequence. Control "inactive" ribozyme M1-B was constructed to contain the same guide sequence and derived from C102 RNA, a M1 mutant that contained point mutations at the active P4 domain abolishing its catalytic activity (Trang, P., Lee, M., Nepomuceno, E., Kim, J., Zhu, H. & Liu, F., Proc Natl Acad Sci USA 97, 5812-7). To determine if M1GS ribozyme with an incorrect guide sequence could affect the level of the target mRNA, ribozyme M1-TK1, which was derived from M1 RNA and targeted the HSV-1 thymidine kinase (TK) mRNA (Trang, P., Lee, M., Nepomuceno, E., Kim, J., Zhu, H. & Liu, F., Proc Natl Acad Sci USA 97, 5812-7), was also used in the analysis. We observed in vitro cleavage of a M80.5 mRNA substrate by M1-A, but not M1-B or M1-TK1 (FIG. 1C, lanes 2-4). The binding affinity of M1-B to the substrate ($K_d$=0.32±0.05 nM), as assayed in triplicate experiments, is similar to that of M1-A ($K_d$=0.36±0.05 nM). Since M1-B contains the same antisense guide sequence and exhibits similar affinity to the M80.5 mRNA sequence as M1-A but is catalytically inactive, this ribozyme can be used as a control for assessing the antisense effect in our experiments.

We cloned DNA sequences encoding M1-A, M1-B, and M1-TK1 into vector pU6, which contains the small nuclear U6 RNA promoter for expressing ribozyme and a green fluorescence protein (GFP) expression cassette (Bertrand, E., Castanotto, D., Zhou, C., Carbonnelle, C., Lee, N. S., Good, P., Chatterjee, S., Grange, T., Pictet, R., Kohn, D., Engelke, D. & Rossi, J. J., Rna 3, 75-88). The pU6-M1GS constructs were transformed into *Salmonella* strain SL101 for gene delivery studies. SL101 was derived from auxotrophic strain SL7207 (Hoiseth, S. K. & Stocker, B. A., Nature 291, 238-9) and in addition, contained a deletion of ssrA/B genes. SL7207 is attenuated in virulence and pathogenesis in vivo and has been shown to function as a gene delivery carrier for the expression of several transgenes in mammalian cells (Paglia, P., Terrazzini, N., Schulze, K., Guzman, C. A. & Colombo, M. P., Gene Ther 7, 1725-30) (Yang, N., Zhu, X., Chen, L., Li, S. & Ren, D., Cancer Biol Ther 7, 145-51) (Bai, Y., Li, H., Vu, G., Gong, H., Umamoto, S., Zhou, T., Lu, S. & Liu, F., Proc Natl Acad Sci USA 107, 7269-7274). SsrA/B regulates the expression of *Salmonella* Pathogenicity Island-2 (SPI-2) genes, which are important for *Salmonella* intracellular survival in macrophages and virulence in vivo (Walthers, D., Carroll, R. K., Navarre, W. W., Libby, S. J., Fang, F. C. & Kenney, L. J., Mol Microbiol 65, 477-93.). Deletion of ssrA/B is expected to further reduce the virulence of *Salmonella* and facilitate intracellular lysis of bacteria and release of the transgene construct, leading to efficient expression of the delivered gene in target cells. The presence of the ribozyme sequence did not affect the viability of the bacterial carrier as we observed no difference in the growth kinetics of *Salmonella* carrying no constructs or various pU6-M1GS constructs in LB broth (FIG. 2A). When cultured in vitro, neither the GFP nor M1GS transcript was detected in *Salmonella* carrying ribozyme constructs, suggesting that M1GS, which was under the control of the U6 promoter, was not expressed in *Salmonella*. When mouse J774 macrophages were infected with *Salmonella* carrying pU6-M1GS constructs, more than 80% of cells were GFP-positive at 24 hours post-infection, demonstrating efficient gene transfer mediated by *Salmonella*. Northern analysis confirmed M1 GS expression in these cells (FIG. 2B). The level of M1GS RNAs in cells treated with SL101 carrying pU6-M1-A was about 3-fold higher than those with SL7207 carrying the same construct (FIG. 2B, lanes 2-3), suggesting that SL101 is a more effective delivery vector, possibly as a result of more efficient intracellular lysis of *Salmonella* and release of pU6-M1-A due to the deletion of ssrA/B, leading to a higher level of gene expression.

Inhibition of MCMV gene expression and growth in cultured cells by *Salmonella*-mediated gene delivery of M1GS sequence. To determine the effect of *Salmonella*-mediated delivery of M1GS on MCMV gene expression, we first treated J774 cells with SL101 carrying ribozyme constructs. The *Salmonella*-containing cells were then isolated by FACS analysis based on GFP expression and infected with MCMV. The expression levels of M80.5/PR mRNAs were determined by Northern analyses. The level of the 7.2 kb long viral transcript (7.2 kb RNA), whose expression is not regulated by M80.5 or PR under the assay conditions (Mocarski, E. S., Shenk, T. & Pass, R. F., Fields Virology pp. 2701-2772), was used as an internal control for the quantitation of expression of M80.5/PR mRNAs (FIG. 3A). At 48 hours post-infection, a reduction of 81±6% and 81±8% in the level of the target M80.5 and PR mRNA was observed in cells treated with SL101 carrying pU6-M1-A while no significant reduction was observed in cells with SL101 containing pU6-M1-B or pU6-M1-TK1 (FIG. 3A and Table 1). The protein expression of M80.5 was determined using Western analysis with the expression of actin as the internal control. A reduction of 85% in the protein level of M80.5 was detected in cells treated with SL101 carrying pU6-M1-A (FIG. 3B). A low level of inhibition (~7-8%) was found in cells treated with SL101 carrying pU6-M1-B (Table 1), presumably due to an antisense effect because M1-B exhibited similar binding affinity to the target sequence as M1-A but was catalytically inactive. Inhibition of M80.5/PR expression is not expected to affect the expression of other viral genes, including immediate-early (α), early (β), and late (γ) genes (Mocarski, E. S., Shenk, T. & Pass, R. F., Fields Virology pp. 2701-2772). To determine if this is the case, the levels of the mie1 (an α transcript) and m155 mRNA (a γ transcript) were examined using Northern analyses while the levels of viral protein M112, a viral early-late (βγ) protein and M99, a viral late (γ) protein were assayed with Western analyses. We observed no significant difference in the levels of these genes among *Salmonella*-treated cells (Table 1), suggesting that the *Salmonella*-mediated delivery of M1-A specifically inhibits the expression of its target, and does not affect overall viral gene expression.

*Salmonella*-mediated gene delivery of anti-M80.5 ribozyme also effectively inhibited MCMV growth. In these experiments, mouse macrophage J774 cells were first treated with SL101 carrying the ribozyme sequences. The *Salmonella*-containing cells were then isolated by FACS analysis based on GFP expression, and infected by MCMV at an multiplicity of infection (MOI) of 1. The infected cultures were harvested at 1-day intervals through 5 days post-infection and viral titers of these samples were determined. At 4 days post-infection, a reduction of at least 2,500-fold in viral yield was observed in cells treated with *Salmonella* carrying pU6-M1-A, while no significant reduction was found in cells treated with SL101 containing pU6-M1-B or pU6-M1-TK1 (FIG. 3C).

Inhibition of MCMV infection and pathogenesis in mice by *Salmonella*-mediated oral delivery of M1 GS sequence. Immunodeficient SCID mice are extremely susceptible to MCMV infection and represent an excellent animal model for evaluating therapeutic approaches designed to block CMV infection and prevent viral associated diseases in vivo (Mocarski, E. S., Shenk, T. & Pass, R. F., Fields Virology pp. 2701-2772). To study *Salmonella*-assisted delivery of M1GS in vivo, we intragastrically inoculated SCID mice with SL101 carrying pU6-M1GS constructs. Gene delivery mediated by SL101 was efficient in vivo as substantial amounts of M1 GS and GFP-positive cells were detected in the liver and spleen of the *Salmonella*-treated mice (FIG. 4A). M1 GS expression was also detected in the lung of these animals (FIG. 4A). Furthermore, SL101 exhibited much less virulence in vivo than the parental strain SL7207 and a wild type strain ST14028s. All mice infected with SL101 ($1 \times 10^9$ CFU/mouse) remained alive even after 70 days postinoculation (FIG. 4D). In contrast, mice inoculated with a much lower dose of ST14028s (1×10³ CFU/mouse) and SL7207 (5×10⁵ CFU/mouse) died within 7 and 15 days, respectively (FIG. 4D). Thus, SL101 appeared to be efficient in gene transfer and exhibited little virulence/pathogenicity in vivo.

Figure 4B:
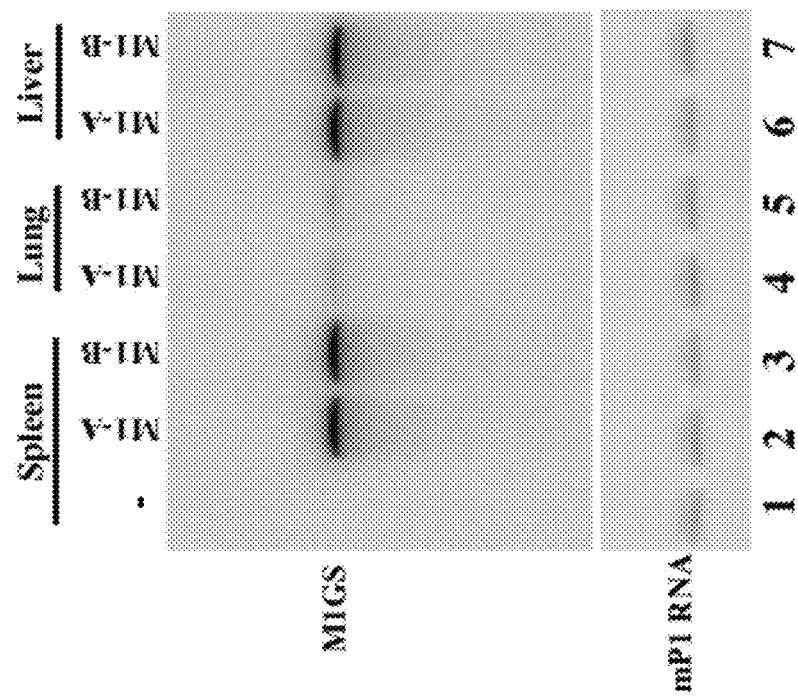
FIG. 4D Virulence and toxicity of *Salmonella* in SCID mice. SCID mice (5 animals per group) were infected intragastrically with ST14028 ($1\times10^3$ CFU), SL7207 ($5\times10^5$ CFU), or SL101 ($1\times10^9$ CFU) carrying pU6-M1-A, and their survival was recorded.
Figure 5A:
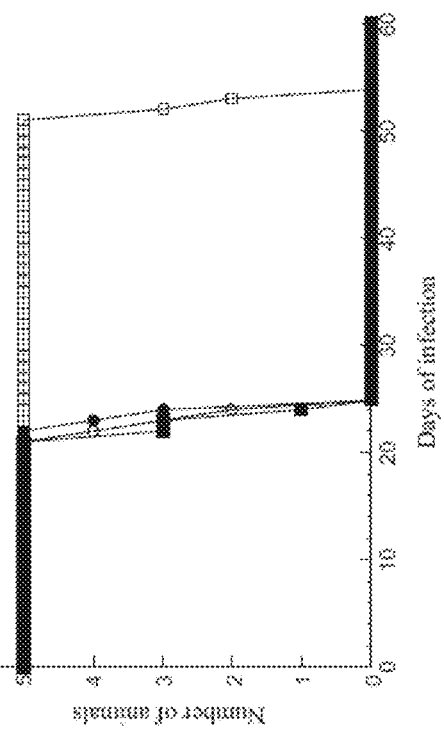
FIG. 5A Mortality of the SCID mice infected with MCMV, followed by oral inoculation of *Salmonella* SL101 ($1\times10^8$ CFU/animal) carrying pU6 (SL101), pU6-M1-A (M1-A), pU6-M1-B (M1-B), or pU6-M1-TK1 (M1-TK1). SCID mice (5 animals per group) were infected intraperitoneally with $1\times10^4$ PFU MCMV, 36 h prior to *Salmonella* inoculation. Oral inoculation of *Salmonella* was repeated every 5 days.
Figure 5B:
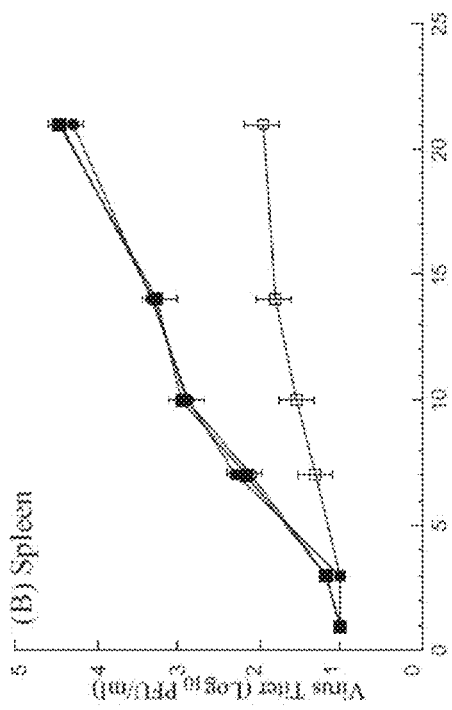
FIG. 5B-FIG. 5C Titers of MCMV in the spleen FIG. 5B and liver FIG. 5C of the infected SCID mice. At different time points post-infection, the animals were sacrificed. Spleens and livers were collected, and the viral titers in tissue homogenates were determined. The limit of detection was 10 PFU/ml of the tissue homogenate. The viral titers represent the average obtained from triplicate experiments. The error bars indicate the standard deviation. Error bars that are not evident indicate that the standard deviation was less than or equal to the height of the symbols.
Figure 5C:
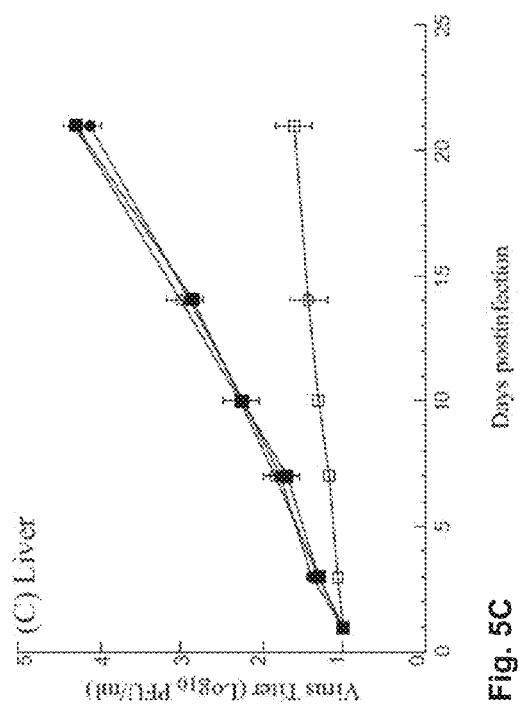

To study the antiviral effect of *Salmonella*-assisted oral delivery of M1GS in vivo, SCID mice were intraperitoneally infected with MCMV, followed by oral inoculation of *Salmonella* carrying ribozyme constructs 36 hours later. To further allow sustained expression of M1GSs, we repeated oral inoculation of *Salmonella* every 5 days until the experiments were terminated. Three sets of experiments were carried out to study the effect of *Salmonella*-mediated delivery of M1GSs on MCMV virulence and infection in vivo. First, the survival rate of the animals was determined. Treatment of SL101 carrying pU6-M1-B or pU6-M1-TK1 had no effect on animal survival compared with untreated animals as all mice died within 25 days post-infection with MCMV (FIG. 5A). In contrast, in MCMV-infected mice treated with SL101 expressing M1-A, life span improved significantly as no animals died within 50 days post-infection (FIG. 5A). Second, viral replication in various organs of the animals was studied during a 21-day infection period before the onset of mortality of the infected animals. At 21 days post-infection, the viral titers in the spleen and liver of animals treated with pU6-M1-A-containing SL101 were lower than those from animals receiving SL101 carrying control constructs by 400 and 600 fold, respectively (FIG. 5B-C). Third, viral gene expression in the tissues was also examined. At 14 days post-infection, substantial expression of viral M80.5/PR mRNAs as well as M80.5 protein was readily detectable in livers and spleens of mice receiving SL101 carrying pU6-M1-B and pU6-M1-TK1, while little expression of M80.5/PR was detected in mice treated with SL101 carrying pU6-M1-A (FIG. 4B-C). Thus, *Salmonella*-assisted oral delivery of M1GS blocked MCMV infection in the treated mice.

Discussion

For nucleic acid-based gene interfering agents such as M1GS ribozyme to be successful as a therapeutic tool for practical applications, a central issue is the targeted delivery of these agents to specific tissues and cells in vivo. To our best knowledge, this study represents the first to demonstrate targeted delivery of M1GS RNAs in animals by *Salmonella*. In this study, we have constructed a M1GS RNA targeting the overlapping region of MCMV M80.5 and PR mRNAs. Furthermore, we have generated a novel attenuated strain of *Salmonella*, SL101, which exhibited high gene transfer activity and low cytotoxicity/pathogenicity in vivo. The ribozyme cleaved the target mRNAs efficiently in vitro and furthermore, reduced their expression levels by 80-85% and inhibited viral growth by 2,500-fold in cells that were treated with SL101 carrying pU6-M1-A. When MCMV-infected SCID mice were orally inoculated with SL101 carrying different M1GS sequence, the expression of M1GS RNAs was detected in several tissues including spleen, liver, and lung. All MCMV-infected animals that received SL101 only or SL101 carrying pU6-M1-B or pU6-M1-TK1 died within 25 days post-infection while those receiving SL101 carrying pU6-M1-A remained alive until 50 days post-infection. Furthermore, viral titers found in the spleens and livers of the animals receiving SL101 carrying pU6-M1-A were significantly lower than those in animals that received SL101 only or SL101 with pU6-M1-B or pU6-M1-TK1. M1-TK1 targets an unrelated mRNA and M1-B is catalytically inactive and contains the identical guide sequence to M1-A. Thus, the observed reduction in MCMV gene expression and growth in the cells and animals that were treated with *Salmonella* carrying pU6-M1-A is primarily attributed to the specific targeted cleavage by the ribozyme as opposed to the antisense effect of the guide sequence or other non-specific effects such as potential immune responses induced by SL101.

Our results also suggest that the *Salmonella*-mediated gene transfer is efficient and that M1GS RNAs expressed following the *Salmonella*-mediated gene delivery are active and specific in mice. First, targeted gene transfer of the ribozyme constructs by SL101 yields substantial expression of ribozyme in cultured cells and in different organs of animals, suggesting efficient gene transfer in vitro and in vivo. Second, the ribozymes expressed following transfer specifically inhibited the expression of M80.5/PR. Only the levels of the target M80.5/PR but not other viral genes examined (e.g. mie1, M99, M112, and m155) were reduced in cells treated with SL101 carrying pU6-M1-A (Table 1). Third, the viability and gene transfer ability of the *Salmonella* vectors were not significantly affected by the presence of ribozyme sequences (FIG. 2). Furthermore, animals that received SL101 carrying M1GS constructs via oral inoculation at over 1×10⁹ CFU exhibited no adverse signs for at least 70 days (FIG. 4D), suggesting that oral inoculation of SL101 and the expression of ribozymes exhibited little pathogenicity or cytotoxicity in vivo. Fourth, ribozyme M1-A expressed following the SL101-mediated gene delivery appeared to be active in cleaving its target mRNA in animals. Reduced M80.5/PR expression, decreased viral titers, and increased survival were observed in mice that were inoculated with SL101 carrying pU6-M1-A but not control constructs pU6-M1-B or pU6-M1-TK1. These results suggest that *Salmonella*-mediated oral delivery of M1GS for cleavage of its target mRNA is effective and specific in vivo in inhibiting the expression of the target mRNA, leading to blocking viral infection and increasing survival of infected animals.

A fundamental challenge in gene therapy is to develop approaches for delivering genetic material in vivo in a way that is tissue/cell specific, efficient, and safe. As a gene delivery tool, *Salmonella*-based vectors exhibit several unique and attractive features. First, *Salmonella*-based vectors are low cost and easy to prepare. Second, they can be administrated orally in vivo. The oral route of administration is non-invasive and has proved to be successful in terms of efficacy and acceptability in vaccine trials with attenuated *Salmonella* strains (Levine, M. M., Herrington, D., Murphy, J. R., Morris, J. G., Losonsky, G., Tall, B., Lindberg, A. A., Svenson, S., Bagar, S., Edwards, M. F. & et al., *Salmonella typhi*, 541Ty and 543Ty, J Clin Invest 79, 888-902) (Levine, M. M., N Engl J Med 361, 403-5). Third, it is easy and feasible to generate new attenuated mutants with different deletions (e.g. SL101), which can be tolerated even by immunodeficient hosts. Fourth, safety is the first and foremost concern for any gene delivery vector. *Salmonella* is not known to be tumorgenic and intergration of its delivered DNA in the host cell genome has not been reported. Furthermore, the anti-typhoid fever vaccine based on the attenuated *Salmonella* strain Ty21a is one of the few live vaccines licensed for human use, and has been extensively used to immunize both adults and children since the late 1980s (Levine, M. M., Herrington, D., Murphy, J. R., Morris, J. G., Losonsky, G., Tall, B., Lindberg, A. A., Svenson, S., Bagar, S., Edwards, M. F. & et al., *Salmonella typhi*, 541Ty and 543Ty, J Clin Invest 79, 888-902) (Levine, M. M., N Engl J Med 361, 403-5). Thus, attenuated *Salmonella* strains may represent promising gene delivery agents with a favorable safety profile.

It is known that different bacterial components such as lipopolysaccharides (LPS) and unmethylated CpG motifs elicit various immune responses, including activation of TLR4 and TLR9 (Akira, S. & Takeda, K., Nat Rev Immunol 4, 499-511) (Krieg, A. M., Nat Rev Drug Discov 5, 471-84), some of which are beneficial to the host while others are detrimental. To reduce the potential cytotoxicity, mutations can be introduced to bacterial vectors to inactivate specific bacterial components (Clairmont, C., Lee, K. C., Pike, J., lttensohn, M., Low, K. B., Pawelek, J., Bermudes, D., Brecher, S. M., Margitich, D., Turnier, J., Li, Z., Luo, X., King, I. & Zheng, L. M., *Salmonella typhimurium*. J Infect Dis 181, 1996-2002). Alternatively, bacteria carrying transgenes that modulate specific responses can be used (Krieg, A. M., Nat Rev Drug Discov 5, 471-84). Indeed, our newly constructed mutant SL101 was highly efficient for gene delivery while exhibiting little if any virulence or toxicity. These results demonstrate the feasibility of developing novel vector strains exhibiting high gene delivery efficiency and low pathogenecity/toxicity in vivo.

Human CMV causes significant morbidity and mortality in immunoimmature or immunodeficient individuals (Mocarski, E. S., Shenk, T. & Pass, R. F., Fields Virology pp. 2701-2772). MCMV infection of SCID mice represents an excellent animal model to study CMV pathogenesis and to assess the efficacy of novel antivirals for blocking viral infection and virulence. Intraperitoneal infection of SCID mice leads to a biphasic infection, initially with viral infection and replication in the spleen and liver, followed by dissemination of the virus via leukocyte-associated viremia from the spleen and liver to peripheral organs (Mocarski, E. S., Shenk, T. & Pass, R. F., Fields Virology pp. 2701-2772) (Collins, T. M., Quirk, M. R. & Jordan, M. C., J Virol 68, 6305-11) (Katzenstein, D. A., Yu, G. S. & Jordan, M. C., J Infect Dis 148, 406-11). SCID mice are highly susceptible to MCMV, and can succumb to as little as 10 PFU virus, primarily due to liver damage and failure associated with viral lytic replication in the organ (Mocarski, E. S., Shenk, T. & Pass, R. F., Fields Virology pp. 2701-2772) (Katzenstein, D. A., Yu, G. S. & Jordan, M. C., J Infect Dis 148, 406-11). Our results indicate substantial expression of M1 GS RNAs in the liver and spleen of the *Salmonella*-treated animals. Furthermore, MCMV M80.5 expression and titer in the spleen and liver was found to be substantially reduced in mice treated with SL101 carrying pU6-M1-A. These results suggest that the delivery of pU6-M1GS constructs and the subsequent expression of M1GS RNAs in the spleen and liver resulted in the inhibition of viral infection in these two organs, leading to an overall diminished systemic infection and viral dissemination in other organs. The improved survival of animals receiving SL101 carrying pU6-M1-A is likely due to the reduced viral load found in the liver of these animals. This is consistent with the notion that a high level of viral lytic replication and production usually leads to severe damage of hepatic tissues and liver failure, and contributes significantly to MCMV virulence and killing of SCID mice (Mocarski, E. S., Shenk, T. & Pass, R. F., Fields Virology pp. 2701-2772) (Collins, T. M., Quirk, M. R. & Jordan, M. C., J Virol 68, 6305-11) (Abenes, G., Chan, K., Lee, M., Haghjoo, E., Zhu, J., Zhou, T., Zhan, X. & Liu, F., J Virol 78, 6891-9). Thus, our results suggest that oral inoculation of *Salmonella* efficiently deliver M1GS sequence for expression in the spleen and liver, and that *Salmonella*-mediated oral delivery of M1GS can effectively block viral systemic infection and increase host survival by inhibiting viral infection in spleens and livers. Our results suggest the expression of ribozymes in the lung of the *Salmonella*-treated animals. Detailed analyses of the delivery of ribozymes in different tissues in mice should further provide insight into the mechanism of *Salmonella*-mediated gene delivery of M1GS RNA in vivo.

The properties and activities of RNase P ribozyme, as well as the simple design of the guide sequence, make M1GS an attractive and unique gene-targeting agent that can be generally used for antiviral as well as other in vivo applications (Gopalan, V. & Altman, S., The RNA World pp. Chapter 6.1). Our study represents the first to use *Salmonella*-mediated oral delivery of RNase P ribozymes for gene targeting applications in vivo. Future studies, including the generation of novel and more active M1GS through in vitro selection and the construction of new *Salmonella* strains through mutagenesis strategies, should facilitate the development of *Salmonella*-mediated gene delivery of RNase P ribozymes as a promising gene targeting approach for in vivo applications.

Materials and Methods

In vitro studies of ribozymes. The DNA sequence for the M80.5 mRNA substrate was constructed by annealing primers AF25 (5'-GGAATTCTAATACGACTCACTATAG-3') and sm80.5 (5'-CGGGATCCGCCCGACTGAGGTA-GACGCGGTGGTTCATCCTATAGTG AGTCGTATTA-3'), followed by PCR. Mutant ribozyme C102 contains several point mutations (e.g. $A_{347}C_{348} \rightarrow C_{347}U_{348}$, $C_{353}C_{354}C_{355}G_{356} \rightarrow G_{353}G_{354}A_{355}U_{356}$) in the catalytic domain (P4 helix) (Trang, P., Lee, M., Nepomuceno, E., Kim, J., Zhu, H. & Liu, F., Proc Natl Acad Sci USA 97, 5812-7). The DNA sequences that encode ribozymes M1-A and M1-B were constructed by PCR using constructs pFL117 and pC102 (Trang, P., Lee, M., Nepomuceno, E., Kim, J., Zhu, H. & Liu, F., Proc Natl Acad Sci USA 97, 5812-7), which contained the DNA sequences of the M1 and C102 ribozymes, as the templates and primers AF25 and M1m80.5 (5'-CCCGCTCGAGAAAAAATGGTGCGTCTACCTCAG TCGGGTGTGGAATTGTG-3') as 5' and 3' primers, respectively. M1-TK1 was generated from pFL117 (Trang, P., Lee, M., Nepomuceno, E., Kim, J., Zhu, H. & Liu, F., Proc Natl Acad Sci USA 97, 5812-7). Cleavage and binding assays were performed as described previously (Trang, P., Lee, M., Nepomuceno, E., Kim, J., Zhu, H. & Liu, F., Proc Natl Acad Sci USA 97, 5812-7) (Supporting Information).

Expression of ribozymes by *Salmonella*-mediated delivery in cultured cells. *Salmonella* strain SL101 was derived from the auxotrophic *Salmonella typhimurium* aroA strain SL7207 (a gift from Bruce A. D. Stocker (Stanford University, CA, USA)) (Hoiseth, S. K. & Stocker, B. A., Nature 291, 238-9) by deleting the coding sequence of ssrA/B (Supporting Information). *Salmonella* carrying different constructs were obtained by transforming SL101 with plasmid pU6, pU6-M1-A, pU6-M1-B, or pU6-M1-TK1. Construct pU6 contained the GFP expression cassette and the small U6 RNA promoter used for the expression of ribozymes in mammalian cells.

To study gene transfer of ribozyme by *Salmonella* vectors, mouse J774 cells ($1 \times 10^6$ cells/ml) pre-treated with IFN-γ (150 U/ml) (R&D Systems Inc., Minneapolis, Minn.) for at least 12 hours were infected with *Salmonella* opsonized with normal mouse serum at a multiplicity of infection (M01) of 10-20 bacteria/cell. Cultures were centrifuged at 200×g for 5 minutes and incubated at 37° C. for 30 minutes to allow phagocytosis to occur. Culture medium was then replaced with fresh medium containing gentamicin (20 μg/ml) and incubated for the indicated time periods. Cells were harvested and the expression of ribozymes was assayed using Northern analyses (Trang, P., Lee, M., Nepomuceno, E., Kim, J., Zhu, H. & Liu, F., Proc Natl Acad Sci USA 97, 5812-7) (Supporting Information).

Studies of viral gene expression and growth. Mouse J774 cells (approximately $1\text{-}5 \times 10^6$ cells) were first incubated with *Salmonella* carrying different constructs at a MOI of 10-20 bacteria/cell at 37° C. for 30 minutes. The medium was then replaced with fresh medium containing gentamicin (20 mg/ml) and incubated for 8 hours to allow the expression of the ribozymes. The *Salmonella*-containing cells were then subjected to FACS using a FACS Vantage SE sorter (BD Biosciences, San Jose, Calif.), and a population of GFP-positive cells (usually 1-5×10$^5$ cells with a positive fluorescence of >99%) was isolated. The isolated cells were cultured for 4 hours and then either mock-infected or infected with MCMV (a MOI of 0.5-1) for another 8-72 h (Trang, P., Lee, M., Nepomuceno, E., Kim, J., Zhu, H. & Liu, F., Proc Natl Acad Sci USA 97, 5812-7). The expression of specific mRNAs and proteins in infected cells was assayed by Northern and Western analyses, respectively, and inhibition of viral growth in these cells were studied (Trang, P., Lee, M., Nepomuceno, E., Kim, J., Zhu, H. & Liu, F., Proc Natl Acad Sci USA 97, 5812-7) (Supporting Information).

*Salmonella*-mediated gene delivery and MCMV infection in animals. Four to six weeks old CB17 SCID mice (Jackson Laboratory, Bay Harbor, Me.) were infected intraperitoneally with 1×10$^4$ PFU of MCMV and at 36 h post-infection, were inoculated with *Salmonella* intragastrically in oral delivery experiments. For intragastric inoculation of mice, animals were first anesthetized with isoflurane and then intragastrically inoculated with 0.1-0.2 ml phosphate-buffered saline (PBS) containing 1×10$^8$ CFU *Salmonella*, using a gavage needle (Lu, S., Killoran, P. B., Fang, F. C. & Riley, L. W., Infect Immun 70, 451-61). The oral inoculation procedure was repeated every 5 days. The gene delivery efficiency was evaluated by examining the GFP signal of the transfected cells in the tissues using fluorescence microscopy and by detecting the expression of M1GS RNAs in mouse tissues (e.g. livers) using Northern analyses.

The mortality of infected animals (five animals per group) was monitored for at least 60 days post-infection, and the survival rates were determined. Groups of MCMV-infected animals (at least five animals per group) were also sacrificed at 1, 3, 7, 10, 14, and 21 days postinoculation. Spleens and livers were harvested and sonicated as a 10% (wt/vol) suspension in a 1:1 mixture of DMEM medium and 10% skim milk. Viral titers of the tissue samples were determined using plaque assays (Abenes, G., Chan, K., Lee, M., Haghjoo, E., Zhu, J., Zhou, T., Zhan, X. & Liu, F., J Virol 78, 6891-9) (Supporting Information). In gene expression experiments, tissues were homogenized, and the expression of M1GS RNA and viral mRNAs was determined using Northern analyses while the expression of viral proteins was assayed using Western analyses (Trang, P., Lee, M., Nepomuceno, E., Kim, J., Zhu, H. & Liu, F., Proc Natl Acad Sci USA 97, 5812-7) (Abenes, G., Chan, K., Lee, M., Haghjoo, E., Zhu, J., Zhou, T., Zhan, X. & Liu, F., J Virol 78, 6891-9) (Supporting Information).

To determine the virulence and toxicity of *Salmonella*, SCID mice (five animals per group) were intragastrically inoculated with *Salmonella* strain ST14028s (1×10$^3$ CFU), SL7207 (5×10$^5$ CFU), and SL101 (1×10$^9$ CFU) carrying pU6-M1-A. Their mortality was monitored for at least 70 days post-infection, and the survival rates were determined.

TABLE 1

| Viral gene | | Ribozymes | | | |
|---|---|---|---|---|---|
| | class | SL101 | M1-TK1 | M1-A | M1-B |
| mie1 mRNA | α | 0% | 2% | 0% | 0% |
| m155 mRNA | γ | 0% | 0% | 2% | 0% |

TABLE 1-continued

| Viral gene | | Ribozymes | | | |
|---|---|---|---|---|---|
| | class | SL101 | M1-TK1 | M1-A | M1-B |
| M80.5 mRNA | γ | 0% | 0% | 81 ± 6% | 7% |
| PR mRNA | γ | 0% | 1% | 81 ± 8% | 8% |
| M112 protein | β, γ | 0% | 0% | 1% | 0% |
| M99 protein | γ | 0% | 2% | 0% | 0% |
| M80.5 protein | γ | 0% | 0% | 85 ± 7% | 8% |

Materials and Methods

Viruses, cells, and antibodies. The Smith strain of MCMV (ATTC, Rockville, Md.) was grown in NIH3T3 cells (ATCC) or mouse J774 macrophages (ATCC) in Dulbecco's Modified Eagle Medium (DMEM) supplemented with 10% Nu-Serum (BD Biosciences, Bedford, Mass.) as described previously (Abenes, G., Chan, K., Lee, M., Haghjoo, E., Zhu, J., Zhou, T., Zhan, X. & Liu, F., J Virol 78, 6891-9). The antibodies against MCMV proteins were kindly provided by Annette Meyer (Pfizer, Inc., Ann Arbor, Mich.) and John Wu (Promab, Inc., Albany, Calif.). The anti-mouse actin antibody was purchased from Sigma Inc. (St Louis, Mo.).

In vitro cleavage and binding studies of ribozymes. M1GS RNAs and the M80.5 mRNA substrate were synthesized in vitro by T7 RNA polymerase (Promega Inc. Madison, Wis.) following the manufacturer's recommendations and further purified on 8% polyacrylamide gels containing 8M urea. Subsequently, the M1GS RNAs were mixed with the [$^{32}$P]-labeled mRNA substrate. The procedures to measure the equilibrium dissociation constants ($K_d$) of the M1GS-M80.5 complexes were modified from Pyle et al (Pyle, A. M., McSwiggen, J. A. & Cech, T. R., Proc Natl Acad Sci USA 87, 8187-91) and have been described previously (Kilani, A. F., Trang, P., Jo, S., Hsu, A., Kim, J., Nepomuceno, E., Liou, K. & Liu, F., J. Biol. Chem 275, 10611-10622). The values of $K_d$ obtained were the average of three experiments. The cleavage reactions were carried out at 37° C. in a volume of 10 μl for 40 minutes in buffer A (50 mM Tris, pH 7.5, 100 mM NH$_4$Cl, and 100 mM MgCl$_2$) (Kilani, A. F., Trang, P., Jo, S., Hsu, A., Kim, J., Nepomuceno, E., Liou, K. & Liu, F., J. Biol. Chem 275, 10611-10622). Cleavage products were separated in denaturing gels and quantitated with a STORM840 phosphorimager (Molecular Dynamics, Sunnyvale, Calif.).

Construction of *Salmonella* strains. *Salmonella* strain SL101 was derived from the auxotrophic *Salmonella typhimurium* aroA strain SL7207 (a gift from Bruce A. D. Stocker (Stanford University, CA, USA)) (Hoiseth, S. K. & Stocker, B. A., Nature 291, 238-9) by deleting the coding sequence of ssrA/B. The plasmid construct pKan-clone7 was used as template to amplify the DNA fragment to delete ssrA/B in the genome of *Salmonella* SL7207 by homologous targeting. Primers P5 (5'-TGTACTGCGATAGTGATCAAGTGC-CAAAGATTTTGCAACAGGCAACTGGAGGGAAGCA TTCATATGAATATCCTCCTTAGTTC-3') and P3 (5'-CT-GCGTGGCGTAAGGCTCATCAAAATA TGACCAAT-GCTTAATACCATCGGACGCCCCTGGTGT-GTAGGCTGGAGCTGCTT-3') were designed to amplify the kanamycin resistance gene sequence in construct pKan-clone7. The resulting PCR products were transformed into SL7207 carrying plasmid pKD46. The ssrA/B deletion mutant was constructed using the A Red recombinase method (Datsenko, K. A. & Wanner, B. L., Proc Natl Acad Sci USA 97, 6640-5), following the procedures described previously (Lu, S., Killoran, P. B., Fang, F. C. & Riley, L. W., Infect Immun 70, 451-61). The non-polar strain SL101 was selected for its sensitivity to kanamycin and further confirmed using PCR.

Analysis of in vitro growth kinetics of *Salmonella*. Growth kinetics of *Salmonella* in LB broth was analyzed by first inoculating a single colony in 2 ml LB broth and culturing at 37° C. with shaking at 250 RPM overnight (>15 hours) (Su, J., Gong, H., Lai, J., Main, A. & Lu, S., Infect Immun 77, 667-75). An aliquot (~30 µl) of the overnight culture was then inoculated into 3 ml fresh LB broth and cultured at 37° C. and 250 RPM. At time points of 0, 2, 4, 6, 8, 10, 12, 14, 16, and 24 hours after inoculation, an aliquot (~100 µl) of bacterial culture was collected and used for analysis by limiting dilution in 96-well plates, and then plated on LB agar plates to determine their CFU/ml. Each sample was analyzed in triplicate and the analysis was repeated at least three times. The average value of CFU/ml was used to generate the growth curve (Su, J., Gong, H., Lai, J., Main, A. & Lu, S., Infect Immun 77, 667-75).

Northern and Western blot analyses. The RNA and protein samples were isolated from cells and tissues as described previously (Kilani, A. F., Trang, P., Jo, S., Hsu, A., Kim, J., Nepomuceno, E., Liou, K. & Liu, F., J. Biol. Chem 275, 10611-10622). The RNA fractions were separated in 1% agarose gels that contained formaldehyde, transferred to a nitrocellulose membrane, hybridized with the [$^{32}$P]-radiolabeled DNA probes that contained the MCMV DNA sequence or the DNA sequence coding for mouse mP1 RNA, and analyzed with a STORM840 Phosphorimager (Trang, P., Lee, M., Nepomuceno, E., Kim, J., Zhu, H. & Liu, F., Proc Natl Acad Sci USA 97, 5812-7). The DNA probes used to detect M1GS RNAs, mouse mP1 RNA, MCMV 7.2 kb RNA transcript, and M80.5 and PR mRNA were synthesized from plasmids pFL117, pmP1 RNA, pM7.2 KB, and pPR, respectively.

For Western analyses, the polypeptides from cell lysates were separated on SDS/9% polyacrylamide gels cross-linked with N,N"methylenebisacylamide, transferred electrically to nitrocellulose membranes, and stained using the antibodies against MCMV proteins and mouse actin in the presence of a chemiluminescent substrate (GE Healthcare, Sunnyvale, Calif.) (Trang, P., Lee, M., Nepomuceno, E., Kim, J., Zhu, H. & Liu, F., Proc Natl Acad Sci USA 97, 5812-7). The stained membranes were analyzed with a STORM840 phosphorimager. Quantitation was performed in the linear range of RNA and protein detection. The levels of the mouse RNase P RNA (mP1), MCMV 7.2 kb transcript, and mouse actin protein were used as the internal controls in Northern and Western analyses, respectively.

Analysis of the inhibition of MCMV growth by M1GS ribozymes. To determine the level of inhibition of viral growth, $5 \times 10^5$ mouse J774 macrophages were first treated with *Salmonella* carrying different constructs at a MOI of 20 bacteria/cell. At 8 hours posttreatment, the *Salmonella*-containing cells were isolated by FACS analysis based on GFP expression. The isolated cells were incubated for 4 hours and then either mock-infected or infected with MCMV at an MOI of 1. The cells and medium were harvested at 1, 2, 3, 4, and 5 days post-infection. Viral stocks were prepared and their titers were determined by performing plaque assays on mouse NIH3T3 cells (Trang, P., Lee, M., Nepomuceno, E., Kim, J., Zhu, H. & Liu, F., Proc Natl Acad Sci USA 97, 5812-7). The values obtained were the average from triplicate experiments.

Plaque assays to determine the viral titers in tissue samples. Plaque assays were performed in NIH3T3 cells plated overnight in 6-well cluster plates (Costar, Corning, N.Y.). Ten-fold serial dilutions of virus samples were inoculated onto each well of NIH3T3 cells. After 90 minutes of incubation, the cells were washed with DMEM then overlaid with DMEM containing 1% low melt agarose (Sigma, St Louis, Mo.). Viral plaques were counted after 3-5 days under an inverted microscope. Each sample was titered in triplicate, and the titer of the sample was the average of the three values and recorded as PFU/ml of organ homogenate. The limit of virus detection in the organ homogenates was 10 PFU/ml of the sonicated mixture. Those samples that were negative at a $10^{-1}$ dilution were designated a titer value of 10 ($10^1$) PFU/ml.

What is claimed is:

1. A cell infected with the virus with an attenuated *Salmonella* having a deletion in ssrA/B comprising a plasmid construct encoding a targeted M1GS ribozyme that cleaves viral mRNA, wherein viral replication is inhibited.

2. The cell of claim 1, wherein the ribozyme is a functional RNase P-based ribozyme.

3. An attenuated *Salmonella* having a deletion in ssrA/B comprising a plasmid construct encoding a targeted M1GS ribozyme that cleaves viral mRNA, wherein viral replication is inhibited.

4. The cell of claim 1, wherein the virus is a cytomegalovirus.

5. The cell of claim 1, wherein the M1GS ribozyme is targeted to a region accessible to ribozyme binding.

6. The cell of claim 1, wherein the attenuated *Salmonella* is SL101.

* * * * *